United States Patent [19]

Sowers

[11] Patent Number: 4,622,302
[45] Date of Patent: Nov. 11, 1986

[54] PROCESS FOR INDUCING MEMBRANE FUSION UNDER AN ELECTRIC FIELD

[75] Inventor: Arthur E. Sowers, Bethesda, Md.

[73] Assignee: American National Red Cross, Washington, D.C.

[21] Appl. No.: 639,127

[22] Filed: Aug. 9, 1984

[51] Int. Cl.[4] .................... C12N 13/00; C12N 5/00; C12N 15/00
[52] U.S. Cl. ................. 435/172.2; 435/173; 435/240; 935/93; 204/131; 204/DIG. 8; 204/DIG. 9
[58] Field of Search .............. 435/173, 172.2, 240, 435/287, 292, 293, 294; 935/93; 204/131, 242, DIG. 8, DIG. 9

[56] References Cited

U.S. PATENT DOCUMENTS

| | | | |
|---|---|---|---|
| 2,440,472 | 4/1948 | Horner et al. | 435/173 X |
| 2,955,076 | 10/1960 | Gossling | 435/287 X |
| 3,095,359 | 6/1963 | Heller | 435/173 X |
| 4,292,408 | 9/1981 | Zimmermann et al. | 435/173 |
| 4,561,961 | 12/1985 | Hofman | 204/274 X |
| 4,578,168 | 3/1986 | Hofman | 204/272 X |

FOREIGN PATENT DOCUMENTS 0819169  4/1981  U.S.S.R. ............... 435/287

OTHER PUBLICATIONS

Benz et al., The Resealing Process of Lipid . . . , Biochimica et Biophysica Acta, 640; 1981; pp. 169–178.
Zimmermann et al., Electric Field-Induced Cell-to-Cell Fusion; J. Membrane Biol. 67; pp. 165–182 (1982).
Zimmermann et al., Electric Field Induced Cell Fusion; BioTechniques; Sep.–Oct. 1983; pp. 118–122.
Crane; American Biotechnology Laboratory 1, An Electro Cell Fuser; pp. 74–79; 1983.
Zimmermann et al., Electric Field–Mediated Cell Fusion; J. Biol. Phys., vol. 10, 1982; pp. 43–50.
Knutton et al., The Mechanism of Cell–Cell Fusion; TIBS–Oct. 1979; pp. 220–223.
Henderson et al., Three-Dimensional Model of Purple Membrane Obtained by Electron Microscopy; Nature, vol. 257, Sep. 1975; pp. 28–32.
Lucy, "Mechanisms of Chemically Induced Cell Fusion" in Poste et al. (ed.), Membrane Fusion, Elsevier/North-Holland Biomedical Press, 1978, pp. 267–304.
Zimmermann, Biochimica et Biophysica Acta, 694, (1982), pp. 227–277.
Neumann et al., The EMBO Journal, vol. 1, No. 7, 1982, pp. 841–845.

Primary Examiner—Sidney Marantz
Assistant Examiner—Randall E. Deck
Attorney, Agent, or Firm—Holman & Stern

[57] ABSTRACT

A device and process for inducing membrane fusion under an electric field. The process comprises the steps of (a) suspending said membranes in an aqueous buffered medium in a manner so that the membranes are without contact with each other; (b) altering said membranes to a fusogenic state by applying 2–30 pulses of direct current at a rate of 2 to 5 pulses per second in an electrical field strength of about 500–1000 volts/mm in the medium, said pulses having a rapid rise time not exceeding about 10 micro seconds and an exponential decay half time of about 0.2 milliseconds to about 1.2 milliseconds; and (c) thereafter bringing said fusogenic membranes in contact with each other. A long-lived metastable fusogenic state of membranes can be obtained by the device and process.

8 Claims, 7 Drawing Figures

FUSION YIELD (%)

PROCESS FOR INDUCING MEMBRANE FUSION UNDER AN ELECTRIC FIELD

BACKGROUND

1. Technical Field

The present invention is related to an apparatus and a process for fusion of cell membranes. More particularly, the present invention is related to an improved device and a method of inducing fusion of cell membranes under the influence of an electric field.

Fusion is defined as the merger or coalescence of at least two cell membranes, spaces or cavities to form a single cellular entity. Fusogenic state is defined as an altered, storable state of the membranes induced by first exposing the membranes to a direct current treatment as described herein infra. It is significant to note that once the membranes are altered to the fusogenic state in accordance with the present invention, all that is then required to induce fusion per se is simply to bring the fusogenic membranes in contact with each other by any suitable means e.g., centrifugation, packing by increasing density, exposure to pulses of alternating current and the like, whereby fusion takes place spontaneously without any further treatment. Furthermore, the fusogenic membranes could be held in this altered state for substantial periods of time up to several minutes prior to fusion, which may allow various manipulations of these fusogenic membranes, e.g. by exposure to chemicals, pharmaceuticals, microorganisms, gene-altering substances and the like. Other advantages of the invention would be apparent to those skilled in the art.

2. Prior Art

Fusion has been induced in many membrane systems using procedures involving electric fields. The state of the art has been reviewed by *Zimmermann et al.* 1983, *Biotechniques* 1, 118–122; *Crane* 1983, *American Biotechnology Laboratory* 1, 74–79; *Zimmermann et al.* 1982, *J. Biol. Phys.* 10, 43–50; and *Zimmermann* 1982, *Biochim. Biophys. Acta.* 694, 227–227, which are incorporated herein by reference. In general, membranes in suspension are fused by first exposing the suspension to a lower strength alternating current (AC) which causes the membranes to come in close proximity with each other as they line up in the so-called "pearl-chain" formation. This phenomenon has been named dielectrophoresis. (*Zimmermann et al.* 1982, *J. Memb. Biol.* 67, 165–182). Fusion is then induced by the application of a higher strength direct current (DC) pulse.

The present invention is quite different from the prior art techniques. In accordance with the present invention, a fusogenic state can be created in separate and individual biological membranes by a treatment with exponentially decaying electric field pulses. The membrane fusion properties of this state are fundamentally different from currently understood membrane fusion phenomenology using electric fields.

Although in a certain aspect of the process, the prior art and the present invention both use pulses which have similar electric field strengths in the membrane suspension medium (500–1000 V/mm), the quality and characteristics of the pulse waveform used is quite different. Whereas the prior art uses a square waveform, i.e., a very rapid risetime and a very rapid fall time, the present invention uses an exponentially-decaying pulse, i.e., a very rapid risetime and an exponentially-decaying fall time. Hence, even in this respect the timescale or "length" of the two different kinds of pulses are not comparable.

Membrane fusion and fusion-associated phenomena are of interest because of their involvement in biological processes. However, the mechanism of fusion is not fully understood. Therefore, creating specific experimental conditions so as to reproducibly manipulate or control the membrane fusion process is not currently possible. For example, fusing membranes to mix membrane components having different origins or for delivery of certain substances to a recipient cytoplasm or internal aqueous compartment cannot be always accomplished by the present state of the art for the simple reason that a delayed interval of time for holding the altered membranes in a fusogenic state was not heretofore possible.

The present invention offers an improved device and a process for inducing fusogenic state which allows fusion and its manipulation in a manner not heretofore possible.

SUMMARY OF THE INVENTION

It is, therefore, an object of the present invention to provide an improved membrane fusion device and process.

It is a further object of the present invention to provide a device and method for fusion of membranes without first holding said membranes in contact with each other.

It is yet another object of the present invention to provide a device and method for fusion of separate spaces enclosed by separate membranes into one space without first holding said membranes in contact with each other.

A further object of the present invention is to produce membranes in a storable fusogenic state.

It is a still further object of the present invention to manipulate fusion and allow storage or suspension of altered or fusible state of membranes for a substantial period of time prior to fusion.

Another object of the present invention is to make it possible to alter the sequence and quality of electric fields from that conventionally known in the art and to provide an improved fusion technology.

Other objects and advantages will become apparent as the description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1A:
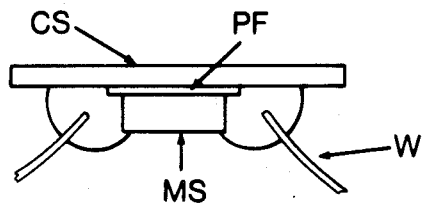
FIG. 1 shows a fusion slide in accordance with the present invention. (A) Fusion chamber made by heat sealing a microslide (MS), with parafilm (PF), in a dry mounting press, to a cover slip (CS); (B) fusion chamber mounted with tape (T), in a frame made from glass strips cut from a standard microscope slide and cemented together with epoxy cement (E). Wire electrodes (W) are anchored to the frame with epoxy cement.

These and other objects and advantages of the present invention are achieved by a device and a process for inducing fusion of cell membranes comprising the steps of (a) suspending said membranes in an aqueous buffered medium in a manner so that the membranes are without contact with each other; (b) altering said membranes to a fusogenic state by applying 2-30 pulses of direct current at a rate of 2 to 5 pulses per second, in an electrical field strength of about 500-1000 volts/mm in the membrane suspension, said pulses having a rapid rise time not exceeding about 10 microseconds and an exponential decay half time of about 0.2 milliseconds to about 1.2 milliseconds; (c) thereafter bringing said fusogenic membranes in contact with each other.

For the practice of this invention, any membrane suitable for fusion can be used. Examples of suitable membranes are erythrocyte ghost membranes, blood platelet plasma membranes, and the like. Furthermore, contrasted with the conventional process wherein only perfect spherical cell membranes could be fused, the present invention allows the use of either spherical, odd-shaped or near-spherical membranes as described herein infra.

For suspending the membranes, any suitable suspension medium generally used for suspending cell membranes can be used. Suitable suspension media are those having a buffer concentration ranging from about 20-150 mM and having a pH value ranging from about 4 to 10. A preferred suspension medium comprises a 30 mM sodium phosphate buffer, pH 8.5.

For preparing a fusion slide and/or a fusion chamber, any electrically nonconducting, preferably transparent material, e.g. glass, clear plastics material and the like could be used.

Preferred embodiments of the present invention are now described below.

DESCRIPTION OF THE PREFERRED EMBODIMENTS

Materials and Methods

Human whole blood collected in plastic bags containing citrate-phosphate dextrose-adenine as anticoagulant was obtained from the Washington, D.C., American Red Cross Regional Blood Center. Packed red cells were obtained by centrifugation at $300 \times g$ for 10 minutes. Packed red cells were washed at least once in isotonic sodium phosphate buffer (pH 7.4), hemolyzed in 5 mM sodium phosphate buffer and washed and stored overnight in 20 mM sodium phosphate buffer as a pellet. All steps were carried out at 0°-4° C. and pH 8.5 unless otherwise indicated.

Working membrane suspensions were made the next day by diluting ghost membranes to 1/10 of pellet concentration by adding 9 volumes of a 30 mM sodium phosphate buffer (pH 8.5).

Ghost membranes were labeled by adding 0.05 ml of a stock solution of the fluorescent dye 1,1'-dihexadecyl-3,3,3'',3'-tetra-methylindocarbocyanine perchlorate, DiI(C-16), in ethanol (3.5 mg/ml) to 4.45 ml of ghost membrane suspension in the desired buffer. Excess dye was removed by one or two washes in buffer at the desired ionic strength. Membranes were dehydrated by washes in buffers containing specified glycerol concentrations (v/v).

Ghost cytoplasmic compartments were labeled by adding 1.0 ml of a solution (1.5 percent w/v) of 10 Kd average M.W. FITC-dextran in 20 mM phosphate buffer to 1.0 ml of a red cell ghost pellet from red cells freshly hemolysed at 0°-° C. and washed as above, warming to room temperature (RT) for two hours, and then washing twice with the desired buffer at room temperature and resuspension of the final pellet to a working suspension with 9 ml of the desired buffer at room temperature.

Figure 1B:
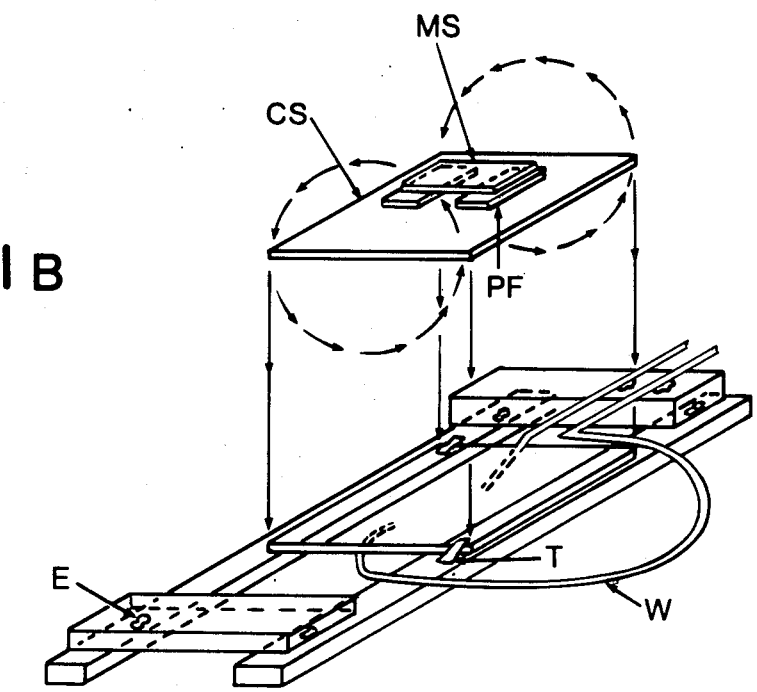

The fusion slide is illustrated in FIG. 1. Membrane fusion chambers were made from a microslide (ca. 10 mm long×2 mm wide) cut with a diamond scribe from a standard 25 mm×75 mm glass microscope slide and a standard #1 thickness (22 mm×22 mm) standard microscope cover glass. The microslide and cover slip were attached to each other as shown with Parafilm or the like using a dry mounting press or double stick tape (FIG. 1a). Any other similar arrangement could also be used. This assembly was, in turn, attached with tape to the fusion slide with the chamber positioned in the center of the rectangular well such that the two wire electrodes were positioned on each side of the microslide and between the strips of tape holding the microslide to the cover glass (FIG. 1b). The wire electrodes are made of solder-tinned #22 gauge copper hookup wire. Electrodes of other conducting material could also be used. Enough membrane suspension was added to one side of the microslide to make a droplet which flooded the wire electrode and filled the chamber by capillary wicking. Continuity of the membrane suspension with the other electrode was completed by adding a droplet to the other side of the microslide such that it flooded the other electrode and coalesced with the suspension in the space between the microslide and the cover glass. The whole assembly was inverted and placed on the microscope stage.

Figure 2:
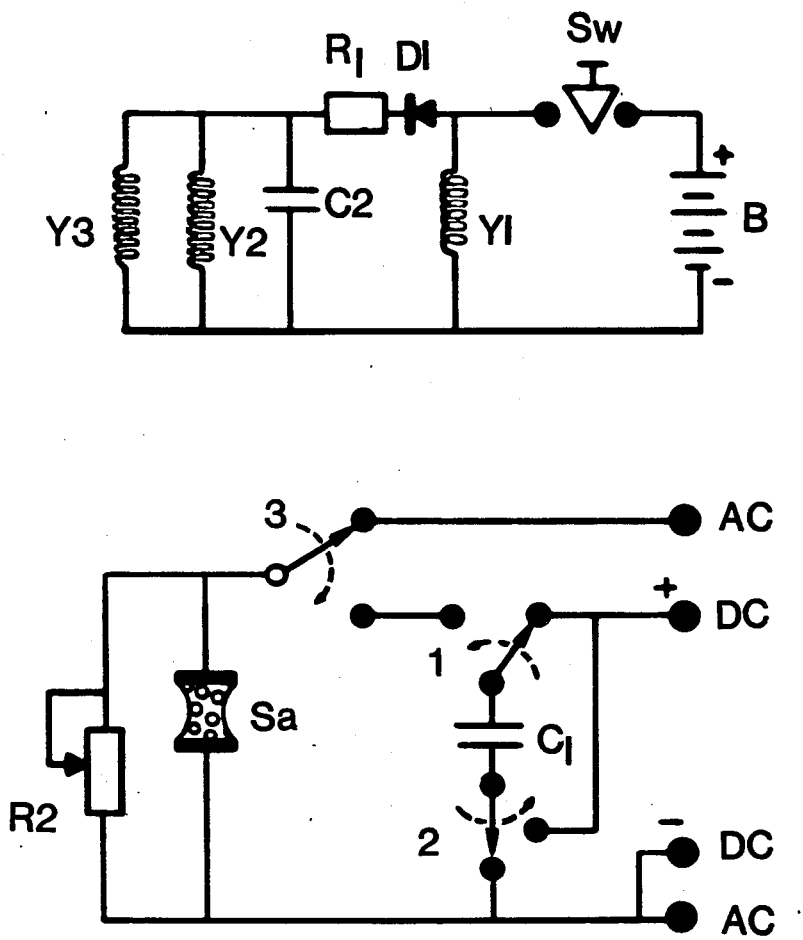
FIG. 2 shows electrical circuit used between an alternating current source (AC), and a direct current source (DC), and the sample (Sa) membrane suspension contained within the fusion chamber. Circuit involves switch contacts (1), (2), and (3) and normal positions of mercury-wetted relays (Clare HGSM 5009, or equivalent) used to connect the AC or the DC to the sample. Capacitor, C1, is a 0.1 uF unit (Plastic Capacitors, Inc., Type 0F50-104, or equivalent). Variable auxillary load resistance, R2, is a variable resistor covering the range 2000Ω to 200,000Ω. Battery (B) is a 9-volt transistor battery and provides the energy, upon pressing switch (SW) to activate relay electromagnets Y1, Y2, and Y3 such that the respective switch arms 1, 2, and 3 are moved in the direction of the dashed arrows but with arm 1 moving sooner than 2 and 3 through a delay introduced by a 51Ω resistor (R1), and a 500 uF capacitor C2 (Sprague type TVA 1315). Diode, D1, (any silicon diode) forces contact 1 to switch back to the starting position before contacts 2 and 3 when switch (SW) is released. All parts were obtained from Newark Electronics, 5026 Herzel Place, Beltsville, Md. 20705.

Electrical currents were fed to the wire electrodes using a circuit shown in FIG. 2. All AC used was from the secondary of an isolation transformer with a 1:1 turns ratio and fed with a variable voltage transformer (0-130 V) supplied with power from a 60 Hz AC power line. In accordance with previous reports of electric field-induced fusion, randomly distributed ghost membranes lined up in the pearl-chain formation in the fusion chamber with the membranes in close proximity to each other within 5-15 seconds after the application of the AC which generated a calculated field strength of 7-15 V/mm. Direct current pulses producing an electric field strength of 500 or 700 V/mm and decay half-times of 0.2, 0.6, or 1.2 msec were applied at the rate of two per second after the pearl-chains were formed.

All DC used was from a variable-voltage (0-1000 V) electrophoresis-type power supply. The chosen AC and DC voltages were applied to the input terminals of the circuit shown in FIG. 2. The rate of discharge of the capacitor, and therefore the rate of decay of the pulse, was controlled independently of the dimensions of the fusion chamber and the electrical conductivity of the membrane suspension by a variable resistance connected in parallel with the fusion chamber. The pulse voltage was monitored by sampling electrodes which were separate from the electrodes used to deliver current to the fusion medium. The samples of the pulse voltage signal were fed into the high impedance input of a differential amplifier using an operational amplifier. The pulse current was monitored by sampling the voltage drop across a resistor connected in series with the fusion chamber current. Both the voltage and current waveform were recorded on a storage screen oscilloscope. Pulse decay half-times were measured from traces on the oscilloscope, screen.

All microscopy and micrography were conducted with phase contrast optics on a Zeiss Model 16 microscope with a MC63 camera system. Illumination was by a tungsten light source or a Zeiss Microflash III xenon strobe lamp for phase images or an epi 100 w Hg light source for flourescence images. For flourescence, a Zeiss No 487709 filter set was used. Kodak 2415 recording film (developed in HC110, dilution A) or Kodak VR1000 (developed in Unicolor K2 process) were used for recording the phase contrast or fluoresence images, respectively.

The fluorescent lipid-soluble dye, DiI, was obtained from Molecular Probes, Junction City, Oreg. All other reagents were obtained from Sigma Chemical Company, St. Louis, Mo.

RESULTS

Figure 3:
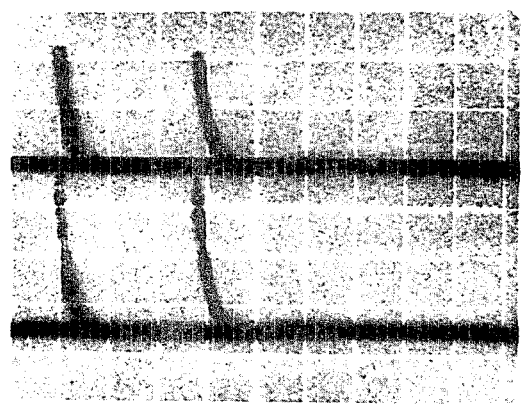
FIG. 3 shows recorded voltage pulse waveform (lower trace 150 V/div) and associated current pulse waveform (upper trace $5 \times 10^{-4}$ A/div) using 30 mM buffer (pH 8.5) in the fusion slide chamber and a shunt resistance of $7 \times 10^{+4}\Omega$. Horizontal scale is 2.0 msec/div.

Oscilloscope traces showed that the pulse voltage ascended to the peak voltage within about 50 $\mu$s (FIG. 3). The pulse voltage then decayed to zero with an approximate half-time, depending on the auxillary load resistance and medium conductivity, of from 0.2 ms to 1.2 ms. Pulse current followed the corresponding voltage waveform. The conductivity of the medium as derived from the voltage and the current waveform was estimated to be about $2 \times 10^{-3} \Omega^{-1}mm^{-1}$ for the buffers used. If converted entirely to heat and undiminished by conductive cooling to the chamber walls, the maximum amount of energy deposited within the membrane suspension volume contained by the fusion chamber would cause a temperature rise in the fusion medium of no more than about 0.3° C. per pulse. All other combinations yielded a lower temperature rise per pulse. Strips of test paper capable of indicating 0.5 pH unit or less dipped into the reservoir pool on each side of the fusion chamber showed no more than a 0.5 pH difference in pH even after extensive application (<100) of direct current pulses with the longest decay half-time available.

Figure 4:
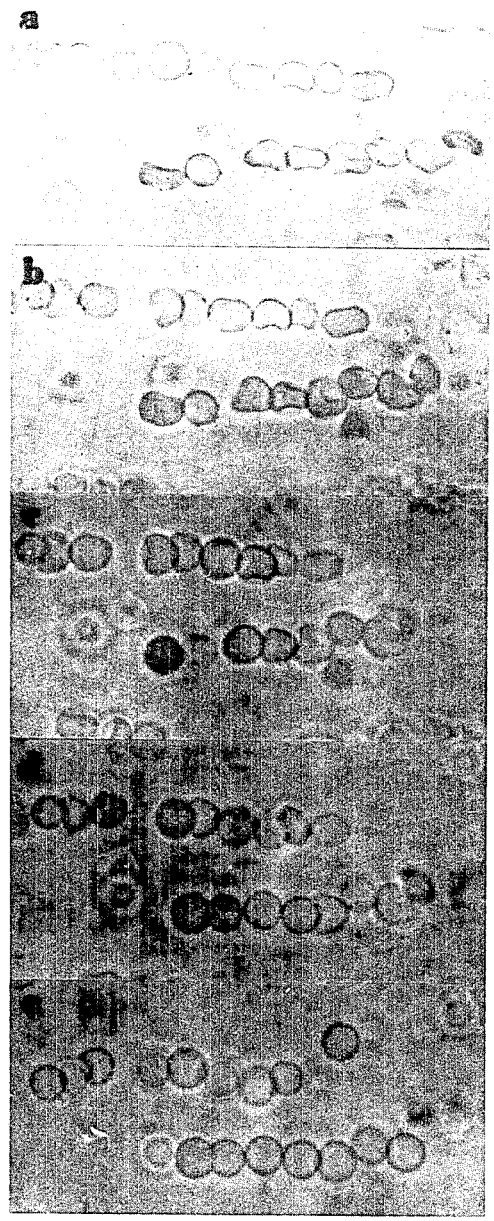
FIG. 4 shows observations by phase contrast optics. Alignment into pearl chains and fusion of red cell ghost membranes in 30 mM Pi buffer (pH 8.5): a, ghosts held in pearl chain formation; b, same ghosts 1.0 second after application of one fusion-inducing pulse (500 V/mm peak field strength, 0.2 msec decay half time); c, same ghosts after one additional (two total) pulse and six seconds after a; d, same ghosts after one additional (three total) pulse and 8.5 seconds after a; e, same ghosts after two additional (five total) pulses and 13 seconds after a. Note progressive change of odd shaped ghosts to perfect or near perfect spheres, single fusion event, and minor repositioning of membranes due to Brownian motion. Photo width is 95 um.

Ghost membranes suspended in 30 mM phosphate buffer generally had shapes including spheres, highly collapsed spheres, and odd shapes (echinocytes and stomatocytes). It was observed that the positions of all membranes within the boundaries of the fusion chamber changed such that the pearl-chain formation was achieved shortly (10-15 seconds) after the application of the AC, in the frequency range of about 40 Hz to 10 Khz and an electric field strength of about 7-25 V/mm, regardless of the shape of those membranes. Application of increasing numbers of the DC pulses which induced fusion were observed to first induce progressive changes in the shapes of all odd-shaped and variably collapsed spherical ghost membranes to perfect spheres before fusion was observed (FIG. 4). Conversion of odd-shaped membranes to perfect spherical membranes always occurred before pulse induced lumens could be seen. Membranes which were spherical before the pulses were applied also fused following the application of the pulse. Membranes closer to the spherical geometry required fewer consecutive pulses to become spheres than membrane which were more highly collapsed. Complete conversion of all membranes to spherocytes required the fewest number of pulses when the pulses had a decay half-time (optimum) which resulted in the maximum fusion yield and required more pulses when the decay half-time was longer or shorter than optimum. These results were independent of whether the DC pulses were delivered to the membrane suspension as fast as two per second, or as slow as one per 10 seconds.

Figure 5:
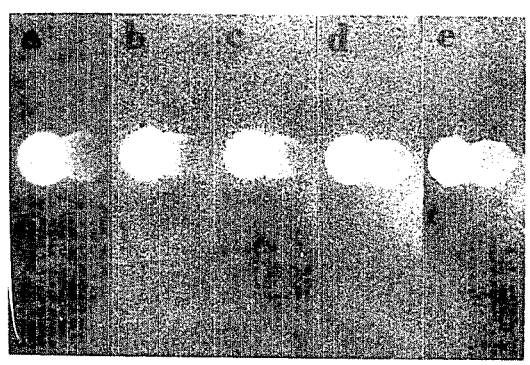
FIG. 5 shows observations by fluorescence of DiI. Movement of fluorescence from labeled membrane (left member) to unlabeled membrane (right member) following fusion events between membrane pairs: a, distinct lumen is visible at 19 seconds after fusion in 100 percent aqueous medium; b-e, a distinct lumen is not visible at 7.5 (b), 19 (c), 35 (d), or 50 (e) seconds after fusion in 10 percent glycerol. Note that right member of pair starts sequence as an odd shape and ends sequence as a slightly elliptical shape. Photo widths are 20 μm.

The application of fusion-inducing pulses to membrane suspension containing both DiI-labeled and unlabeled membranes resulted in the time-dependent lateral diffusion of fluorescence from the labeled to the unlabeled membranes and resulted in the formation of a distinct lumen at the hourglass constriction (FIG. 5a). However, in the presence of glycerol, the membranes exposed to the fusion-inducing pulses showed the movement of DiI from the labled membrane to the unlabeled membrane but without the formation of an observable lumen at the hourglass constriction (FIG. 5b–e).

Figure 6:
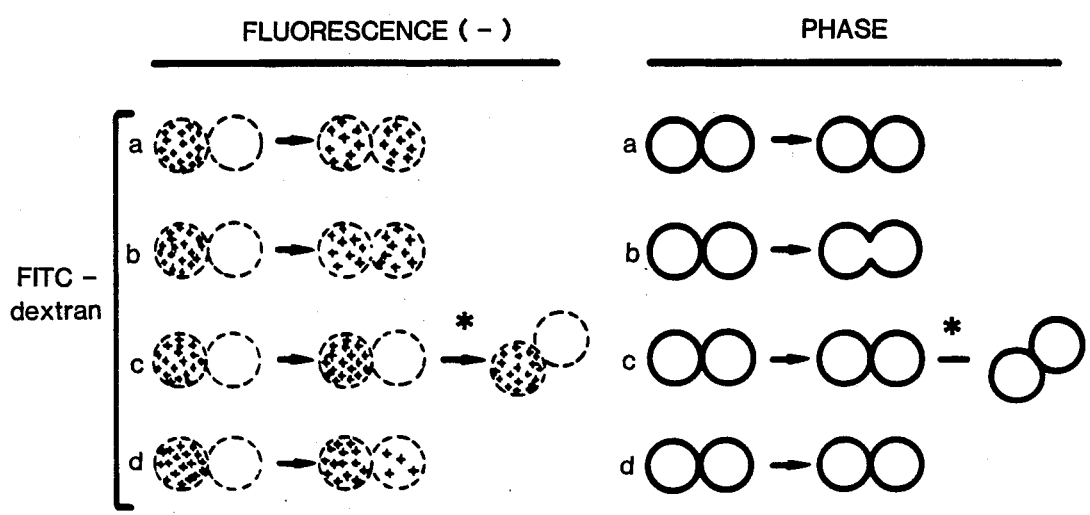
FIG. 6 shows a summary of FITC-dextran monitored and phase optics monitored changes following the application of fusion inducing pulses: a, movement of FITC-dextran from labeled cytoplasmic compartment to unlabeled cytoplasmic compartment to produce uniform labeling without formation of a lumen in phase optics; b, same as a except with the formation of a distinct lumen in phase optics; c no movement of label but physical membrane- membrane connection is indicated by random drift of cylindrical groups at some time after AC is removed; d, partial movement of label from labeled cytoplasmic compartment to unlabeled cytoplasmic compartment to produce a non-uniform labeling pattern in originally unlabeled cytoplasmic compartments.

Application of fusion-inducing pulses to mixtures of resealed membranes having a fluorescent water soluble (FITC-dextran) label in cytoplasmic compartments and unlabeled membranes held in the pearl-chain formation resulted in at least four distinctly observable phases (FIG. 6). First, labeled cytoplasmic compartments became continuous with other unlabeled compartments as the fluorescence became completely and uniformly distributed in the other compartments immediately after the pulses were applied. Viewing the same membrane pearl-chains in phase optics showed the presence of visually distinct lumens in some fused membranes. Second, some pearl-chains showed uniform fluorescence but no visually distinct lumen could be seen by phase optics. Third, some pearl-chains did not show redistribution of the fluorescence to unlabeled compartments but evidently became attached to one another since removal of the AC after the pulses were applied led to randomly oriented pearl-chains with fluorescence in only the originally labeled cytoplasmic compartments. Fourth, the fluorescence in some labeled cytoplasmic compartments moved to unlabeled cytoplasmic compartments only in steps which were discrete as well as simultaneous with each applied pulse. A more uniform distribution of fluorescence was eventually observed with progressively more pulses. Using an electric field strength of 1,000 v/mm and a pulse decay half-time greater than 1.2 msec caused the fluorescence to disappear from the labeled cytoplasmic compartments and appear in the background.

Membranes dehydrated by glycerol permitted fusion to be observed between membranes which were not perfectly spherical (FIG. 5b–e). This is an exception to the observation that fusion occurred only after membranes became spherical upon application of fusion inducing DC pulses.

An increase in glycerol concentration permitted fusion to occur among nonspherical membranes (FIG. 5b–e). This is an exception to the observation that both lumen producing and nonlumen producing phases occurred only when membranes were first converted to the spherical shape as the fusion inducing pulses were applied.

Figure 7:
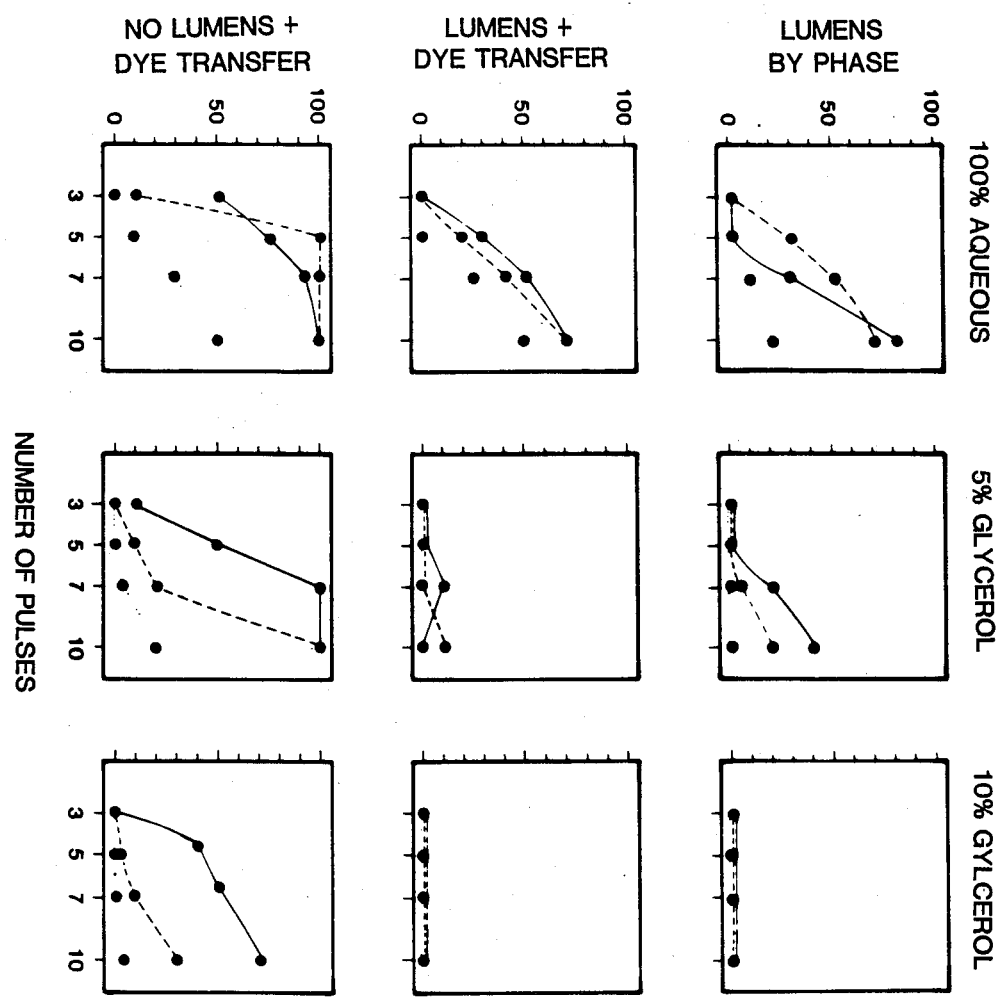
FIG. 7 shows fusion yield (percent on ordinate) as a function of number of pulses (N on abscisa), pulse decay half time (0.2 ms, dotted; 0.6 ms, dashed; 1.2 ms, solid), and presence of glycerol (left column, 0 percent; middle column, 5 percent; right column, 10 percent). Upper row fusion yield based on fraction of all membranes which develop distinct lumens as determined by phase optics (FIG. 4). Middle row fusion yield based on fraction of all labeled membranes in which fluorescent label moves to at least one unlabeled membrane and is accompanied by a distinct lumen (FIG. 5a). Lower row fusion yield based on fraction of all labeled membranes in which fluorescent label moves to at least on unlabeled membrane regardless of whether it is accompanied by formation of distinct lumen (FIG. 5b-e). Peak electric field strength during pulse: 500 V/mm, left column., 700 V/mm, middle and right columns.

The fraction of all membranes in the pearl-chain formation which developed lumens visible by phase optics had a complex dependence on pulse decay half-time, number of pulses, and presence of glycerol (FIG. 7, top row). For the 100 percent aqeous medium, three to seven pulses and a decay half-time of 0.6 msec resulted in the greatest yield. However, the greatest overall yield was obtained with ten pulses with a decay halftime of 1.2 msec. Glycerol generally inhibited (5 percent glycerol) or eliminated (10 percent glyclerol) the yield of lumens and shifted the pulse decay half-time for optimum yield from 0.6 msec to 1.2 msec.

The fraction of DiI labeled membranes in which the label was passed to at least one originally unlabeled membrane was dramatically related to both the production of lumens and glycerol concentration. In general, glycerol almost completely inhibited lumen production (FIG. 7, middle row) but caused only a relatively small reduction in non-lumen producing fusion yield (FIG. 7, bottom row). Addition of glycerol also shifts the pulse decay half-time for highest fusion yield from 0.6 msec to 1.2 msec. A peak electrical field strength of 700 V/mm was used for both glycerol concentrations and 500 V/mm for the 100 percent aqueous medium, because use of the higher field strength on membranes in the 100 percent aqueous medium caused both distortion of the membrane shape and lower yield, while use of the lower voltage in the glycerinated medium resulted in overall and proportionally lower yields.

The application of a subthreshold number of fusion-inducing pulses to membranes held in the pearl-chain formation by the AC followed by removal of the AC and a short wait (1–2 minutes), resulted in randomly oriented membranes and randomly oriented cylindrical groups of spheres with two or more membranes each (FIG. 6).

The fusion slide and circuit used to obtain fusion in red cell ghost membranes have the following advantages compared to prior art systems: First, the fusion slide is simple, inexpensive, contains disposable elements and electrodes which can be easily changed by desoldering and soldering, and permits electric field effects to be observed at a considerably greater (1–2 mm) distance from the electrodes where electrochemical and electrolytic processes may take place than prior art chambers. It can be calculated that at the highest observed three-dimensional translational diffusion coefficients for solution components, a relatively large amount of time (many minutes) is needed before diffusion of electrolysis or electrochemical products from the electrode will arrive at the center of the fusion chamber. The procedure of the present invention allows the use of the commonly available utility power lines as a convenient source of the AC needed to bring about the pearl-chain alignment of membranes.

Whether in terms of lumen-producing events or non-lumenproducing events, fusion yield is critically dependent on the pulse number, the pulse decay rate of the applied pulses and membrane hydration. Pulse decay half-times 0.2–1.2 msec are significantly longer than previously published optimum pulse lengths as described by *Zimmermann et al.* 1983, *Biotechniques* 1, 118–122; *Crane* 1983, *American Biotechnology Laboratory* 1, 74–79; *Zimmermann et al.* 1982, *J. Biol. Phys.* 10, 43–50; and *Zimmermann* 1982, *Biochim. Biophys. Acta.* 694, 227–227.

Although examples where the time-dependent increase in the diameter of some lumens falls short of achieving a final large spherical fusion product, the stability of the image indicates that fusion has occured. Since the appearance of a lumen, however, satisfies the requirements as described by *Knutton et al.* 1979, *Trends Biochem. Sci* 4:220–223 for both cytoplasmic communication and membrane continuity, both membrane events can be designated as fusion. This is consistent with previous reports, and all previous reports of electric field-induced fusion have used this type of visual evidence for fusion. However, the time-dependent and irreversible lateral diffusion of DiI into adjacent unlabeled membranes, and the diffusion of FITC-dextran into adjacent unlabeled cytoplasmic compartments, respectively, demonstrate that membrane-membrane continuity can be produced in some of these electric field-induced membrane fusion events without producing a lumen detectable by either phase contrast or fluorescence imagining of DiI labeled membranes. The fact that non-lumen yielding fusion events account for at least a small but finite fraction and, at most, a large and significant fraction of all fusion events indicates that use of phase contrast optics alone may significantly underestimate the fusion yield. Furthermore, non-lumen producing fusion has important implications for our understanding of fusion phenomenology and cytoskeleton-related stabilization of membrane mechanical properties since the difference between non-lumen and lumen producing fusion events appears to be related to the stability of the connection made between membranes upon fusion.

Although bleaching of FITC-dextran fluorescence prevents photographic documentation and hinders visual scoring of phenomena observed over many minutes, several important observations were made. Two kinds of movement of FITC-dextran were observed in membrane fusion events which do not result in visually discernible outlines of membrane lumens by either phase optics or by the fluorescent membrane label. In the first kind of movement, the fluorescence moved rapidly, completely, and simultaneously with a single pulse to form a chain of polyspheres, all with equal brightness. In the other kind of movement, the first pulse caused a chain of fluorescent spheres to appear: one sphere (the sphere originally containing the label) much brighter than the others, and others uniformly dim. Successive pulses resulted in successively less difference in the fluorescence intensity between the bright sphere and the dim spheres until all spheres showed uniform fluorescence. It is obvious that the first kind of movement was due to the formation of a relatively large and permanent pore or lumen or a transient pore or lumen with a relatively long halflife (e.g. hundreds of msec). In the second kind of movement, the fluorescence moved rapidly but in discrete portions or increments which were simultaneous (within the limits of human reaction time) with each of several applied pulses. Without being bound to any theory; it is hypothesized that this kind of movement indicates that reversible transient connections between cytoplasmic compartments are formed only during passage of the current pulse through the membrane suspension. Conversely, the pore or lumen must be small enough or short lived enough to prevent substantial equilibration of the concentration of the label among the originally unlabeled cytoplasmic compartments. The presence of distinct lumens by phase contrast optics in fused membranes which showed uniform fluorescence was, of course, an obvious and self consistent observation. On the other hand, an occasional cylinder of spheres adhering to one another was observed which still showed fluorescence in only one of the membranes in the cylinder after several fusion-inducing pulses were delivered to the suspension. It is not known as to why these few membranes were resistant to fusion. However, removal of the AC after the pulses were delivered resulted in the drift of cylindrical groups of spheres away from the parallel formation and towards a random distribution of membranes. This indicates that the pulses caused some sort of molecular rearrangement of the membrane which resulted in the membranes becoming attached to each other without (1) breaking or permeabilizing the membrane (no FITC dextran loss from the cytoplasmic compartment to the suspension medium), (2) causing a fusion-related connection of labeled with unlabeled membranes (no lateral diffusion of DiI), or (3) causing cytoplasmic communication (FITC dextran movement into unlabeled cytoplasmic compartments). Since the adhering spheres remain in a cylindrical form indefinitely, it may be possible that the glycocalyx and an intact cytoskeletal system are involved. A totally fluid membrane would otherwise result in randomly clumped aggregates rather than linear arrays.

Without being bound to any theory or hypothesis, and using the figure of 1.5 pm$^3$/d as described by Henderson et al. 1975 Nature 257:28–32 and the average molecular weight for FITC-dextran (=10 Kd), a molecular volume of 15 nm$^3$ and a molecular diameter of 3 nm is calculated for the connections. Hence, the transient connections between cytoplasmic compartments must have a lumen diameter larger than 3 nm for FITC-dextran to move into unlabeled compartments and close to 3 nm, or any value smaller, when the transient connection is closed (resealed). It is significant that this figure is close to the 4 nm diameter calculated indirectly in previous measurements on electric field-induced pores in reversible membrane breakdown experiements, *Benz et al.* 1981, *Biochim. Biophys. Acta.* 640:169–178. Moreover, it should be pointed out that non-lumen containing cylindrical arrays of spheres showing uniform fluorescence in all member sphere cytoplasmic compartments after one or more pulses do not allow a conclusion to be made about whether the cytoplasmic connections are in a stable open (d>3 nm) or a stable closed (d<3 nm) state. Nevertheless, both the membrane continuity and the cytoplasmic communication criteria for fusion were demonstrated in membrane events both with and without a large (d>2 μm), unmistakable lumen. Therefore, the former is referred as lumen-producing fusion and the latter as non-lumen- producing fusion. Since lumen-producing fusion could be strongly inhibited by glycerol in 30 mM phosphate buffer, it is possible that membrane hydration may play a role in the membrane event which causes a microscopic lumen to become unstable and develop into a macroscopic lumen in which the diameter increases in a time dependent manner. Although a role for membrane hydration in artificially induced fusion events has been previously discussed, *Lucy et al. Elsevier/North Holland Biomedical press.* 267–304, it is not well understood. In any case, the data indicate that lumen production is functionally separate from the process of fusion.

Lastly, the fact that both types of fusion can be observed if fusion-inducing pulses are applied to a suspension of membranes in the absence of AC and then, after a period of 1–3 minutes, followed by the application of the AC to bring the membranes into a pearl-chain formation suggests that the pulses induce fusion by a mechanism which destabilizes the membrane. Also this destablized state has a comparatively long lifetime (minutes) compared to the time needed for fusion to occur (seconds or fractions of a second). The present invention provides the first direct evidence that a long-lived metastable fusogenic membrane state can be induced with a non-chemical stimulus.

Intact red cells in isotonic phosphate buffer (pH 7.4) can be fused in the same chamber with the same electric pulse circuit described here if a concentration is used which results in a monolayer of cells in physical contact after the cells are allowed to settle to the bottom of the fusion chamber by gravity and more pulses are used.

Lumens in lumen-producing fusion events are generally first noticeable by phase optics not sooner than 15–30 seconds after the end of a train of fusion-inducing pulses are applied to a suspension of membranes. Examining a large number of membranes for lumens by phase optics requires that relatively little time can be spent looking at invidual membranes for the subtle change which shows up as a small lumen. Hence, large fusion yields were often not perceivable until as much as 45 to 90 seconds later. Fusion events could thus be taking place at any time during this interval and therefore not be simultaneous. On the other hand, the start of the movement of the DiI from labeled membranes to the unlabeled membranes could be observed as early as 5–10 seconds after the end of a train of pulses and the degree of penetration of the label into the unlabeled membranes can be used to estimate, by back extrapolation, when the fusion events took place. The observation of instantaneous (within human reaction time) pulse-induced movement of the FITC-dextran from labeled cytoplasmic compartment to unlabeled cytoplasmic compartment, however, permits the lower limit for fusion simultaneity to be estimated. Taking the lag time for human perception into account, electric field induced fusion can, in at least a fraction of the membrane present, be now stated to be simultaneous within 100–200 msec.

It is understood that examples and embodiments described herein are for illustrative purposes only and that various modifications or changes in light thereof will be suggested to persons skilled in the art and are to be included within the spirit and purview of this application and the scope of the appended claims.

What is claimed is:

1. A process for inducing fusion of cell membranes comprising the sequential steps of (a) suspending cell membranes in an aqueous buffered medium so that the membranes are without contact with each other; (b) altering said membranes to a fusogenic state by applying 2–30 pulses of direct current at a rate of 2 to 5 pulses per second in an electrical field strength of about 500–1000 volts/mm in the medium, said pulses having a rise time not exceeding about 10 microseconds and an exponential decay half time of about 0.2 milliseconds to about 1.2 milliseconds; and (c) thereafter bringing said fusogenic membranes in contact with each other.

2. The process of claim 1 wherein step (c) commences after an interval of time subsequent to step (b).

3. The process of claim 1 wherein step (c) commences immediately after step (b).

4. The process of claim 1 wherein said buffered medium has a buffer concentration ranging from about 20–150 mM.

5. The process of claim 4 wherein said buffered medium has a pH value of about 4 to 10.

6. The process of claim 1 wherein the step of bringing said fusogenic membranes in contact comprises applying alternating current.

7. The process of claim 6 wherein said alternating current has a frequency range of about 40 Hz to 10 KHz.

8. The process of claim 7 wherein said alternating current has an electric field strength in the range of about 7–25 volts/mm.

* * * * *